(12) United States Patent
Hirschhorn et al.

(10) Patent No.: US 11,896,266 B2
(45) Date of Patent: Feb. 13, 2024

(54) MULTIHEAD GROOMING AND CLEANING TOOL, PARTICULARLY FOR AN INFANT

(71) Applicant: FRIDABABY, LLC, Miami, FL (US)

(72) Inventors: Chelsea Hirschhorn, Miami, FL (US); Gregory Adam Hack, Aventura, FL (US); Maria V. Level, Miami, FL (US); Samuel Sauceda, El Serino, CA (US); Matthew Saxton, Agoura Hills, CA (US)

(73) Assignee: Fridababy, LLC, Miami, FL (US)

( * ) Notice: Subject to any disclaimer, the term of this patent is extended or adjusted under 35 U.S.C. 154(b) by 884 days.

(21) Appl. No.: 16/895,955

(22) Filed: Jun. 8, 2020

(65) Prior Publication Data

US 2021/0378710 A1    Dec. 9, 2021

(51) Int. Cl.
| | | |
|---|---|---|
| *A61B 17/50* | (2006.01) |
| *A61B 17/24* | (2006.01) |
| *A61B 17/00* | (2006.01) |

(52) U.S. Cl.
CPC .............. *A61B 17/50* (2013.01); *A61B 17/24* (2013.01); *A61B 2017/00473* (2013.01); *A61B 2017/246* (2013.01); *A61B 2503/045* (2013.01)

(58) Field of Classification Search
CPC ..................... A61B 17/50; A61B 17/24; A61B 2017/00473; A61B 2017/246; A61B 17/244; A61B 17/32; A61B 50/00; A61B 50/20; A61B 2050/0056; A61B 2503/045; A61F 11/006; B25F 1/04; B25F 1/00; B25F 1/003; B25F 1/006; B25F 1/02; B25G 1/06; B25G 1/063; B25G 1/08; B25G 1/085; B25B 13/00; B25B 13/10; B25B 13/102; B25B 13/105; B25B 13/107; B25B 23/0007; B25B 23/0035; B25B 23/0042; A45D 29/18; A45D 29/007; A45D 29/04; A45D 29/17; A45D 29/20; A46B 5/0041; A46B 5/0008; A46B 5/0095; A46B 2200/1046; B43K 23/06
USPC .................... 606/162; 132/75.3; 81/489, 490
See application file for complete search history.

(56) References Cited

U.S. PATENT DOCUMENTS

| | | |
|---|---|---|
| 234,378 A | 11/1880 | Pierce |
| 280,849 A | 7/1883 | Nelson |
| 300,858 A | 6/1884 | Feicker |
| 554,046 A | 2/1896 | Billings |
| 631,113 A | 8/1899 | Geiser |

(Continued)

FOREIGN PATENT DOCUMENTS

| | | |
|---|---|---|
| CN | 201790951 U | 4/2011 |
| DE | 20108321 U1 | 8/2001 |
| EP | 1138292 A1 | 10/2001 |

*Primary Examiner* — Brooke Labranche
*Assistant Examiner* — Lauren Dubose
(74) *Attorney, Agent, or Firm* — Perkins IP Law Group LLC; Jefferson Perkins (57) ABSTRACT

A multihead grooming and cleaning tool, particularly for infants, has an elongate handle with two opposed slots. A tool body is housed in each respective slot and rotates around a tool body axis. In a first use configuration, a first tool head is deployed beyond the end of the handle while a second tool head is shrouded by the handle. In a second use configuration, the opposite is the case. Detenting structure in the slot coacts with detenting structure on the tool body to detent the tool body to the first or the second use configuration.

5 Claims, 5 Drawing Sheets

(56) References Cited

U.S. PATENT DOCUMENTS

| | | |
|---|---|---|
| 655,007 A | 7/1900 | Rairigh |
| 676,915 A | 6/1901 | Ridge |
| 696,955 A | 4/1902 | Moser |
| 750,182 A | 1/1904 | Furbish |
| 890,150 A | 6/1908 | Marble |
| 5,251,352 A | 10/1993 | Cullison |
| 5,283,920 A | 2/1994 | Plummer |
| 5,450,775 A * | 9/1995 | Kozak ................. B25G 1/085 |
| | | 81/177.4 |
| 5,509,921 A | 4/1996 | Karell |
| 5,632,756 A | 5/1997 | Kruglick |
| 5,649,942 A | 7/1997 | Yeh |
| 5,706,545 A * | 1/1998 | Yamada ............... A46B 5/0075 |
| | | 15/172 |
| 5,715,850 A | 2/1998 | Markgraaf |
| 5,888,199 A | 3/1999 | Karell et al. |
| 5,897,568 A | 4/1999 | Vanraes |
| 6,128,805 A | 10/2000 | Rivera |
| 6,187,021 B1 | 2/2001 | Wim |
| 6,270,510 B1 | 8/2001 | Westendorf |
| 6,346,113 B1 | 2/2002 | Turri |
| 6,432,117 B1 | 8/2002 | Murray |
| 6,736,826 B2 | 5/2004 | Begun |
| 6,776,786 B2 | 8/2004 | Kim |
| 6,939,360 B2 | 9/2005 | Crespo |
| 7,070,603 B2 | 7/2006 | Eicoff |
| 7,074,230 B2 | 7/2006 | Olson |
| 7,658,745 B2 | 2/2010 | Olson |
| D631,957 S | 2/2011 | Perez et al. |
| 7,951,106 B1 | 5/2011 | Perez et al. |
| D656,609 S | 3/2012 | Perez et al. |
| 8,241,236 B2 | 8/2012 | Yardley |
| 8,402,583 B1 | 3/2013 | Bebber |
| 8,555,031 B2 | 10/2013 | Edme et al. |
| 8,728,107 B2 | 5/2014 | Huttner et al. |
| 8,777,972 B2 | 7/2014 | Burres |
| 9,060,896 B2 | 6/2015 | Lai |
| 9,233,027 B1 | 1/2016 | Jackson |
| 9,278,030 B2 | 3/2016 | Olson |
| 9,480,605 B2 | 11/2016 | Farzin |
| 9,498,383 B2 | 11/2016 | Edme et al. |
| 9,532,793 B2 | 1/2017 | Wilson |
| 9,549,854 B1 | 1/2017 | Crespo |
| 9,826,920 B2 | 11/2017 | Pahuja et al. |
| 9,918,878 B2 | 3/2018 | Burres |
| 10,105,264 B2 | 10/2018 | Trombley |
| 10,154,927 B2 | 12/2018 | Fahn et al. |
| 10,226,554 B2 | 3/2019 | Baker et al. |
| 10,291,951 B2 | 3/2019 | Olson |
| 2006/0085018 A1 | 4/2006 | Clevenger |
| 2007/0193600 A1* | 8/2007 | Garofano ............... A46B 9/021 |
| | | 132/218 |
| 2011/0066172 A1 | 3/2011 | Silverstein |
| 2012/0294666 A1* | 11/2012 | Jang ....................... A46B 17/04 |
| | | 401/126 |
| 2021/0037958 A1* | 2/2021 | Ashley ..................... B44D 3/00 |

\* cited by examiner

MULTIHEAD GROOMING AND CLEANING TOOL, PARTICULARLY FOR AN INFANT

BACKGROUND OF THE INVENTION

Tools have been provided in the past for cleaning, grooming and extracting matter from various orifices of humans, particularly infants. Infants in particular are known to suffer from stopped-up nasal and ear passages. Tending an infant therefore often entails cleaning out these passages and removing dirt and debris from other surfaces of their bodies.

The features of infants are, of course, smaller than their adult counterparts and instruments for removing detritus from their various orifices should be smaller than similar instruments for adults, and smaller than an adult's fingers. They should also be designed so that their application to the infant does not cause trauma. Ideally such instruments for infants have stops or enlargements that prevent undue penetration of a nose, ear, etc. while a cleaning operation is in progress.

U.S. Pat. No. 9,480,605 to Farzin discloses a device for extracting dried nasal mucus or earwax from an infant. The device has an elongate handle with a tool head on each end. In one embodiment, one of the tool heads is a curved loop, while the other of the tool heads is a bowl with an upwardly curved margin. The caregiver may use either of these tool heads in extracting mucus or earwax from the infant. However, the caregiver is restricted to using one of these two tool heads. An improved infant care tool would provide other tool heads for the caregiver to use, while remaining compact.

SUMMARY OF THE INVENTION

According to one aspect of the invention, a multiheaded cleaning and grooming tool is provided for a human, particularly for an infant. The tool has an elongate handle with opposed first and second ends. An elongate first slot opens on the first end and extends inwardly toward the handle center. A first tool body axis extends through the first slot and at an angle to an axis of the handle. An elongate first tool body is mounted in the first slot and has a first tool body end and a second tool body end. The first tool body is rotatable around the first tool body axis. An elongate second slot opens on the second end and extends inwardly toward the handle center. A second tool body axis extends through the second slot and is disposed at an angle to the handle axis. An elongate second tool body is mounted in the second slot, and has a third tool body end and a fourth tool body end. The second tool body is rotatable around the second tool body axis.

In a first use configuration of the first tool body, a first tool head affixed to the first tool body end is deployed beyond the first end of the handle, while a second tool head, affixed to the second tool body end, is shrouded by the handle. In a second use configuration of the first tool body, the second tool head is deployed beyond the first end of the handle, while the first tool head is shrouded by the handle. Similarly, in a first use configuration of the second tool body, a third tool head affixed to the third tool body end is deployed beyond the second end of the handle, while a fourth tool head, affixed to the fourth tool body ends, is shrouded by the handle. In a second use configuration of the second tool body, the fourth tool head is deployed beyond the second end of the handle, while the third tool head is shrouded by the handle.

In another aspect of the invention, a multiheaded cleaning and grooming tool for a human, particularly an infant, is provided. The tool has an elongate handle with first and second handle ends. A first slot is formed to open on the first handle end. A first tool body axis extends from a top surface of the first slot to a bottom surface of the first slot. The first tool body axis is spaced from the first handle end and also from a center of the handle. The first tool body axis is formed at an angle to a handle axis. At least one of the top and bottom surfaces of the slot has formed therein a slot detent structure. The slot detent structure is spaced from the first tool body axis by a first distance.

A first tool body is mounted in the first slot and is adapted to rotate around the first tool body axis. The first tool body has opposed first and second tool body ends. The first tool body has a top surface that extends from the first tool body end to the second tool body end, and a bottom surface that does the same. The top surface of the first tool body is disposed in sliding relation to the top surface of the first slot, while the bottom surface of the first tool body is disposed in sliding relation to the bottom surface of the first slot.

A first tool body detent structure is formed on at least a preselected one of the top and bottom surfaces of the first tool body. The first tool body detent structure is spaced from the first tool body axis by the first distance. Similarly, a second tool body detent structure is formed on the preselected one of the top and bottom surfaces of the first tool body, so as to be spaced from the first axle by the first distance. In a first use configuration, the first tool body detent structure interacts with the first slot detent structure to resist torque applied to the first tool body around the first tool body axis. This keeps the first tool body fixed in the first use configuration until a sufficient amount of torque is applied to overcome the detent interaction. While in the first use configuration, a first tool head, affixed to the first tool body end, is deployed for use in a position beyond the first handle end, while a second tool head, affixed to the second tool body end, is shrouded by the handle.

In a second use configuration, the second tool body detent structure interacts with the first slot detent structure so as to resist torque applied to the first tool body around the first tool body axis. This keeps the first tool body fixed in the second configuration until a sufficient amount of torque is applied to overcome the detent interaction. While in the second use configuration, the second tool head is deployed for use in a position beyond the first handle end while the first tool head is shrouded by the handle.

Preferably, the tool further includes a second slot that opens on the second handle end and extends toward the handle center. The second slot has a top surface and a bottom surface spaced from the top surface. A second tool body axis extends from the top surface of the second slot to the bottom surface thereof, is formed at an angle to the handle axis, and is spaced from both the second handle end and the handle center. A second slot detent structure is formed on at least one of the top surface of the second slot and the bottom surface of the second slot. The second slot detent structure is spaced from the second tool body axis by a second distance.

An elongate second tool body is disposed in the second slot and is adapted to rotate around the second tool body axis. The second tool body has a third tool body end and a fourth tool body end opposed to the third tool body end. A top surface of the second tool body extends from the third tool body end to the fourth tool body end and is disposed in slidable relation to the top surface of the second slot. A bottom surface of the second tool body likewise extends from the third tool body end to the fourth tool body end and is disposed in slidable relation to the bottom surface of the second slot. At least a preselected one of the top surface of the second tool body and the bottom surface of the second tool body has formed thereon a third tool body detent structure. The third tool body detent structure is spaced from the second tool body axis by the second distance. A fourth tool body detent structure is also formed on at least the preselected one of the top surface of the second tool body and the bottom surface of the second tool body, and is spaced by the second distance from the second tool body axis.

In a first use configuration of the second tool body, the third tool body detent structure interacts with the second slot detent structure to resist torque applied to the second tool body around the second tool body axis. This keeps the second tool body fixed in the first use configuration until an amount of torque is applied to the second tool body which exceeds the detenting resistance. While the second tool body is in its first use configuration, a third tool head, affixed to the third tool body end, is deployed to be disposed beyond the handle second end, while a fourth tool head, affixed to the fourth tool body end, is shrouded by the handle. In a second use configuration of the second tool body, the fourth tool body detent structure interacts with the second slot detent structure to resist torque applied to the second tool body around the second axle. This keeps the second tool body fixed in the second use configuration until an amount of torque is applied to the second tool body which exceeds the detenting resistance. While the second tool body is in the second use configuration, the fourth tool head is deployed for use beyond the second handle end, while the third tool head is shrouded by the handle.

In one embodiment, the first, second, third and fourth tool heads may be selected from the group consisting of picks, scoops, straight loops and curved loops. One or more of the tool heads may be formed of a polymer that is harder than one used to mold the tool bod(ies).

In one embodiment, the first and second tool body detent structures comprise respective depressions made in the preselected one of the top and bottom surfaces of the first tool body. In this embodiment, the first slot detent structure includes a bump sized to fit into each of the depressions.

In one embodiment, the first tool body comprises a substrate molded out of a first polymer such as polypropylene and an overmolded component molded out of a second polymer, such as a TPE, that is softer than the first polymer. The depressions forming the first and second body detent structures advantageously may be formed in the overmolded component only.

In one embodiment, the first and second body detent structures are formed on a first one of the top and bottom surfaces thereof. The other, opposed surface of the first tool body may be used as a surface on which an indicium is formed to indicate a suggested for the tool head in question. One such indicium may be placed near the first tool body end while another indicium may be placed near the second tool body end.

In one embodiment, the handle comprises a top half and a separately molded bottom half. A lower surface of the top handle half forms the top surface of the first slot. An upper surface of the bottom handle half forms the bottom surface of the second slot. The top half of the handle is joined to the bottom half of the handle, preferably capturing the rotating tool bod(ies) thereinbetween. The handle halves may each comprise a substrate formed of a first polymer such as polypropylene and an overmolded component formed of a second polymer, such as a TPE, that has a higher coefficient of friction than the first polymer (when solidified). The second polymer may be injected into holes in the handle half substrate so that the overmolded component is mechanically locked to the handle half substrate.

In those embodiments having two tool bodies, the user may freely choose to have the first tool body in its first or second use configuration, and independently may rotate the second tool body to be in its first or second use configuration. In this way, the user may configure the tool to any of four different combinations of tool heads.

BRIEF DESCRIPTION OF THE DRAWINGS

Further aspects of the invention and their advantages can be discerned in the following detailed description as read in conjunction with the drawings of exemplary embodiments, in which like characters denote like parts and in which.

DETAILED DESCRIPTION

Figure 1:
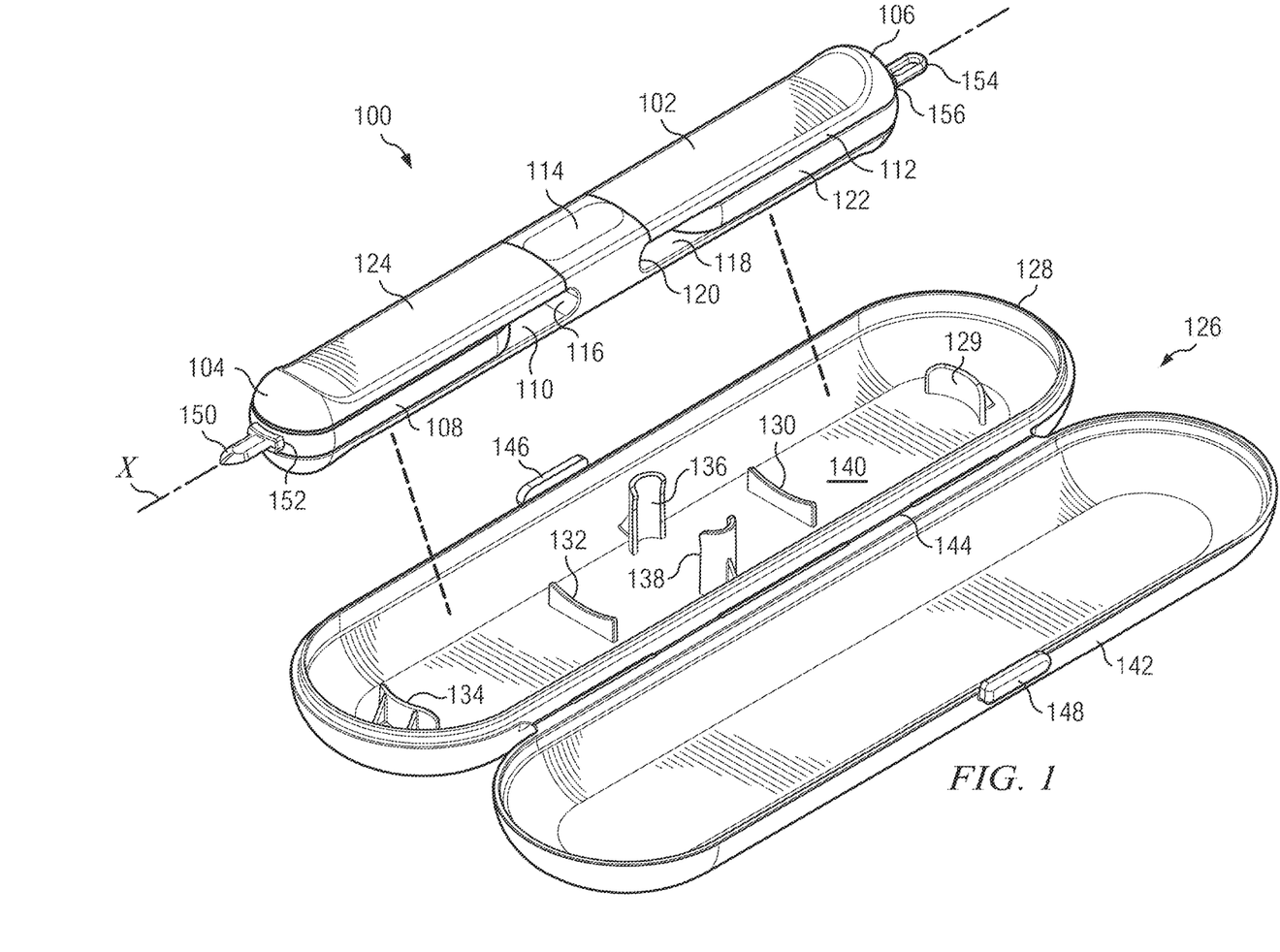
FIG. 1 is a top exploded perspective view of a multihead cleaning and grooming tool according to the invention, and a case in which it may be stored.

One embodiment of a multiheaded cleaning and grooming tool is shown generally at 100 in FIG. 1. The tool 100 has an elongated handle 102 disposed on a handle axis X. Handle 102 has a first handle end 104 and an opposed second handle end 106. An elongate first tool body 108 is mounted in a first slot 110. The first slot 110 is open at first end 104 and to each side (one shown at 112 in this FIGURE) of the handle 102. The first slot 110 proceeds inwardly toward a handle center 114 and terminates at an inner wall 116.

A second slot 118 is open at the second handle end 106 and proceeds inwardly in the opposite direction toward handle center 114. The second slot 118 terminates at an inner wall 120. The second slot is also open at the right side 112 of handle 102 and at the left side (not shown in this FIGURE). An elongate second tool body 122 is mounted in the second slot 118. The handle 102 has a top 124 and a bottom (not visible in this FIGURE) that are connected together by the handle sides.

The tool 100 may be provided with a storage case 126. The interior of a bottom half 128 of the storage case 126 may be provided with supports 129, 130, 132 and 134 to receive the tool 100. Clasps 136 and 138, which may take a semicylindrical form as shown, may be provided to hold the tool 100 in place when contained by storage case 126. The clasps 136 and 138 extend upwardly from an inner floor 140 of the bottom half 128. The bottom half 128 of storage case 126 is connected to a top half 142 of the storage case 126 by a plastic hinge 144, which may be disposed in parallel to axis X. Once the tool 100 is installed in the case 126, its top half 142 may be closed around plastic hinge 144 and snapped shut by the interaction of bottom half closure element 146 and top half closure element 148.

Figure 2:
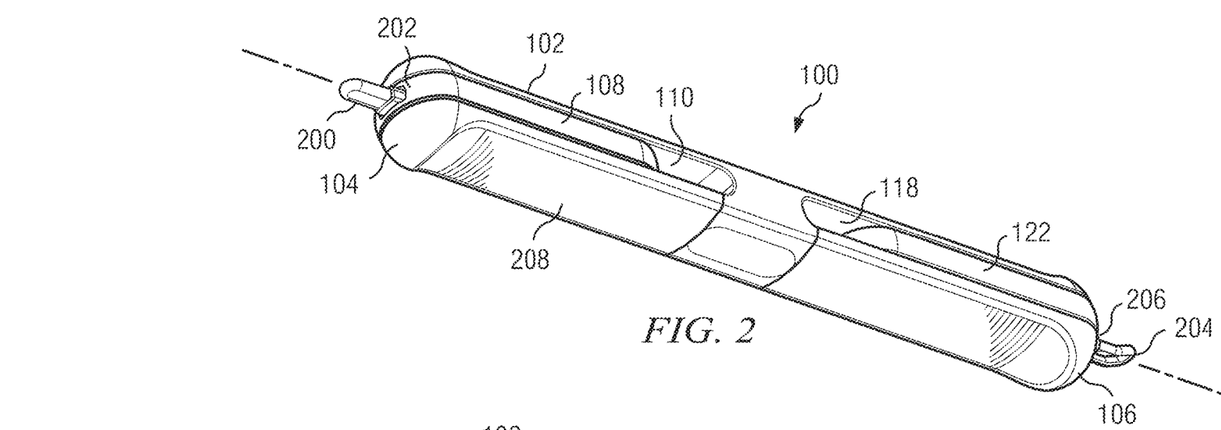
FIG. 2 is a bottom perspective view of the tool shown in FIG. 1, with first and second tool bodies assuming respective second use configurations.

In FIG. 1, the tool bodies 108, 122 are shown in respective first use configurations, in which a first tool head 150 extends from a first tool body end 152 outwardly beyond first handle end 104, and in which a third tool head 154 extends from a third tool body end 156 outwardly beyond second handle end 106. In FIG. 2, the tool bodies 108, 122 are shown in respective second use configurations, in which a second tool head 200 extends from a second tool body end 202 outwardly beyond first handle end 104, and in which a fourth tool head 204 extends from a fourth tool body end 206 outwardly beyond second handle end 106. The tool bodies 108, 122 rotate around respective tool body axes 539 and 545 (see FIGS. 5, 6 and 8) and may be detented to either the first or second use configurations independently of each other, as will be described in further detail below. FIG. 2 further shows a bottom 208 of the handle 102.

Figure 3:
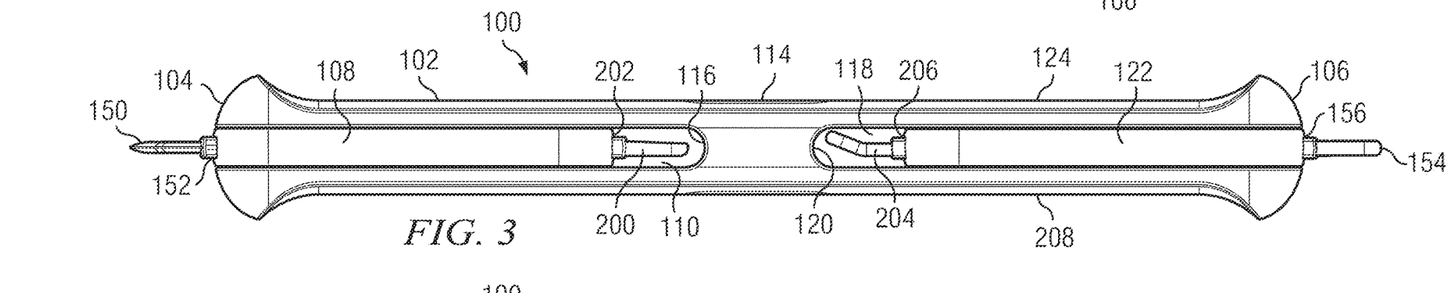
FIG. 3 is a side view of the tool shown in FIGS. 1 and 2, with first and second tool bodies being shown in respective first use configurations.
Figure 4:
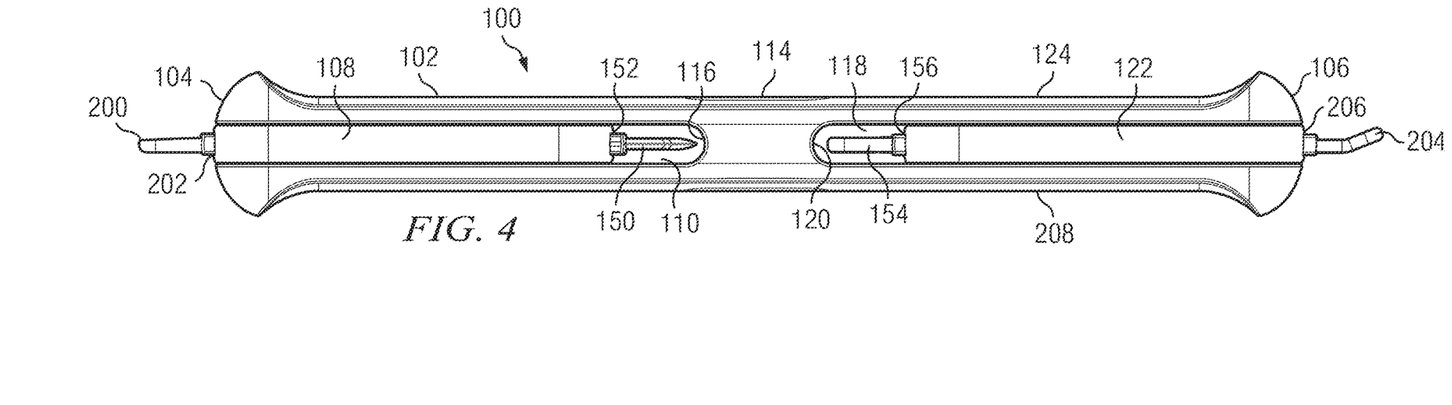
FIG. 4 is a side view of the tool as shown in FIG. 3, but with the first and second tool bodies being shown in respective second use configurations.

The first handle end 104 preferably is enlarged relative to the surface of handle top 124 and handle bottom 208 at more inward locations toward handle center 114, as shown in FIGS. 3 and 4. Throughout most of its length along axis X, the handle 102 has a uniform thickness from its top surface to its bottom surface. This thickness is increased at each handle end 104, 106. The first tool body end 152 has a surface which, when the first tool body 108 is in the first use configuration, conforms to the surface of first handle end 104, with the exception of a small axially extending overmold shutoff surface adjoining tool head 150. Therefore, the combination of first handle end 104 and first tool body end 152 presents a smooth, convexly curved surface that can act as a stop to prevent the overpenetration of tool head 150 into an orifice of the subject when performing a grooming or matter-extracting operation. Similarly, second handle end 106 preferably is enlarged relative to the thickness of most of the rest of the handle 102. Second handle end 106 may, for example, be convexly curved in shape and may match the shape of first handle end 104 for reasons of aesthetics. Alternatively, the shape or outer surface of second handle end 106 intentionally may be different from the shape or surface of first handle end 104, so that the user may quickly discriminate between the two and more easily select a particular tool head for use.

FIG. 3 shows that when the second tool body 122 is in the first use configuration, the third tool body end 156 conforms to the surface of second handle end 106, except for a small overmold shutoff surface immediately adjoining tool head 154. Second handle end 106 and third tool body end 156 therefore present a smooth convexly curved surface that acts as a stop to prevent the overpenetration of tool head 154 into an orifice of the infant or other subject.

When the first tool body 108 is in the first use configuration, its second tool body end 202 and its second tool head 200 will be housed in first slot 110, and in that position will be shrouded by handle 102. Similarly, and as shown in FIG. 3, when the second tool body 122 is in its first use configuration, the fourth tool body end 206 and the fourth tool head 204 will be housed within second slot 118, and in that condition will be shrouded by tool handle 102.

FIG. 4 is a side view similar to that of FIG. 3, but showing first tool body 108 in its second use configuration and showing second tool body 122 in its second use configuration. Tool body 108 and tool body 122 may be independently put in either their first or second use configurations; it is possible for tool body 108 to be in its first use configuration and at the same time for tool body 122 to be in its second use configuration, and vice versa. To change from a first use configuration to a second use configuration, the user applies enough torque to the tool body around its axis that the resistance caused by the relevant detent structures (described below) is overcome, and rotates the currently used tool head to a storage position inside the handle, which rotation will at the same time deploy the other tool head on the tool body to a use position.

In the second use configuration, the second tool body end 202 conforms to the surface of first handle end 104, (except for a small overmold shutoff surface immediately adjacent tool head 200), therefore presenting a smooth convexly curved stop surface to the infant that prevents overpenetration of tool head 200. Similarly, when the second tool body 122 is in its second use configuration, the fourth tool body end 206 conforms to the surface of second handle end 106 (except for a small overmold shutoff surface immediately adjacent tool head 204), thereby presenting a smooth, convexly curved stop surface to the infant that prevents the overpenetration of fourth tool head 204.

Figure 5:
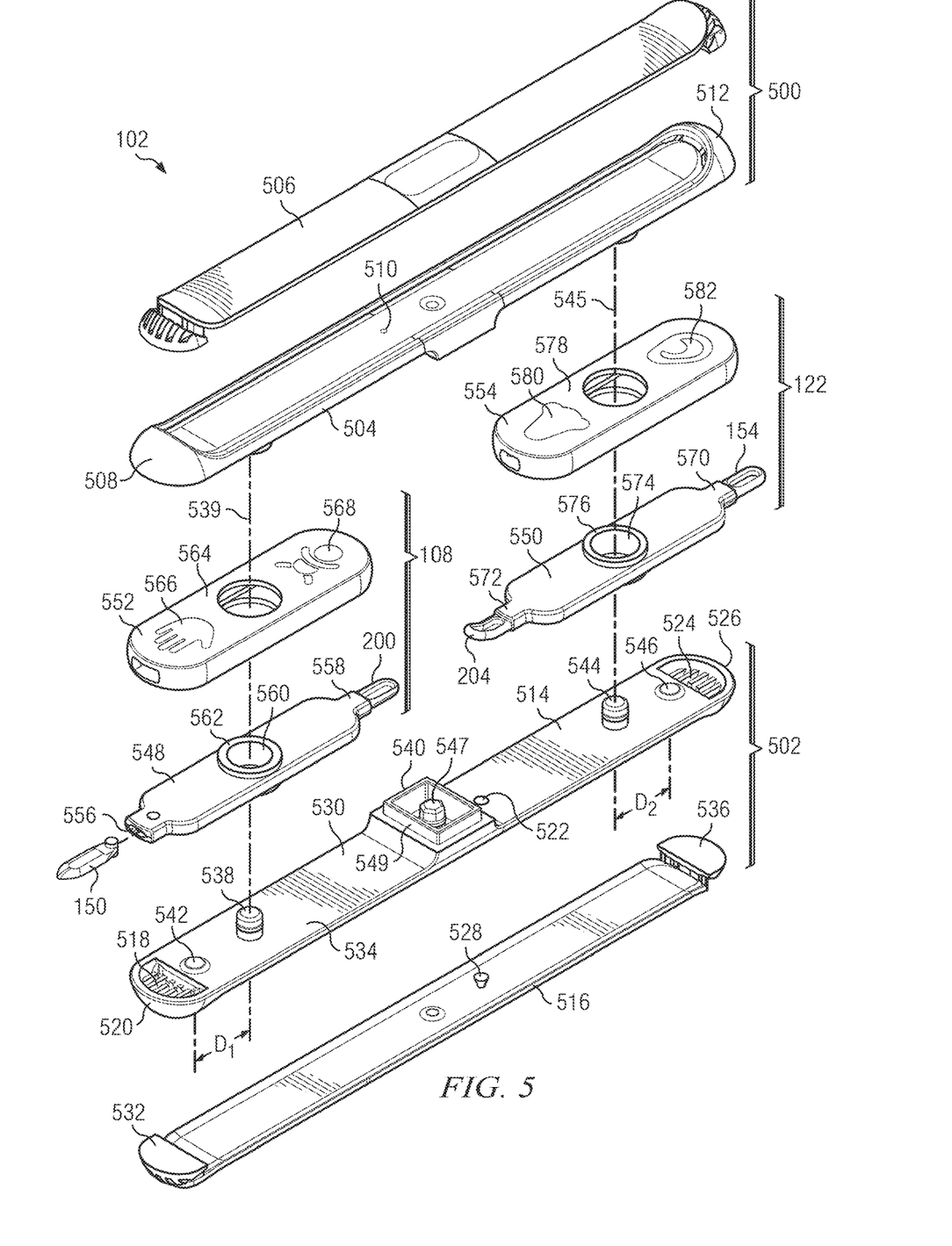
FIG. 5 is a top perspective exploded view of the tool shown in FIGS. 1-4.
Figure 6:
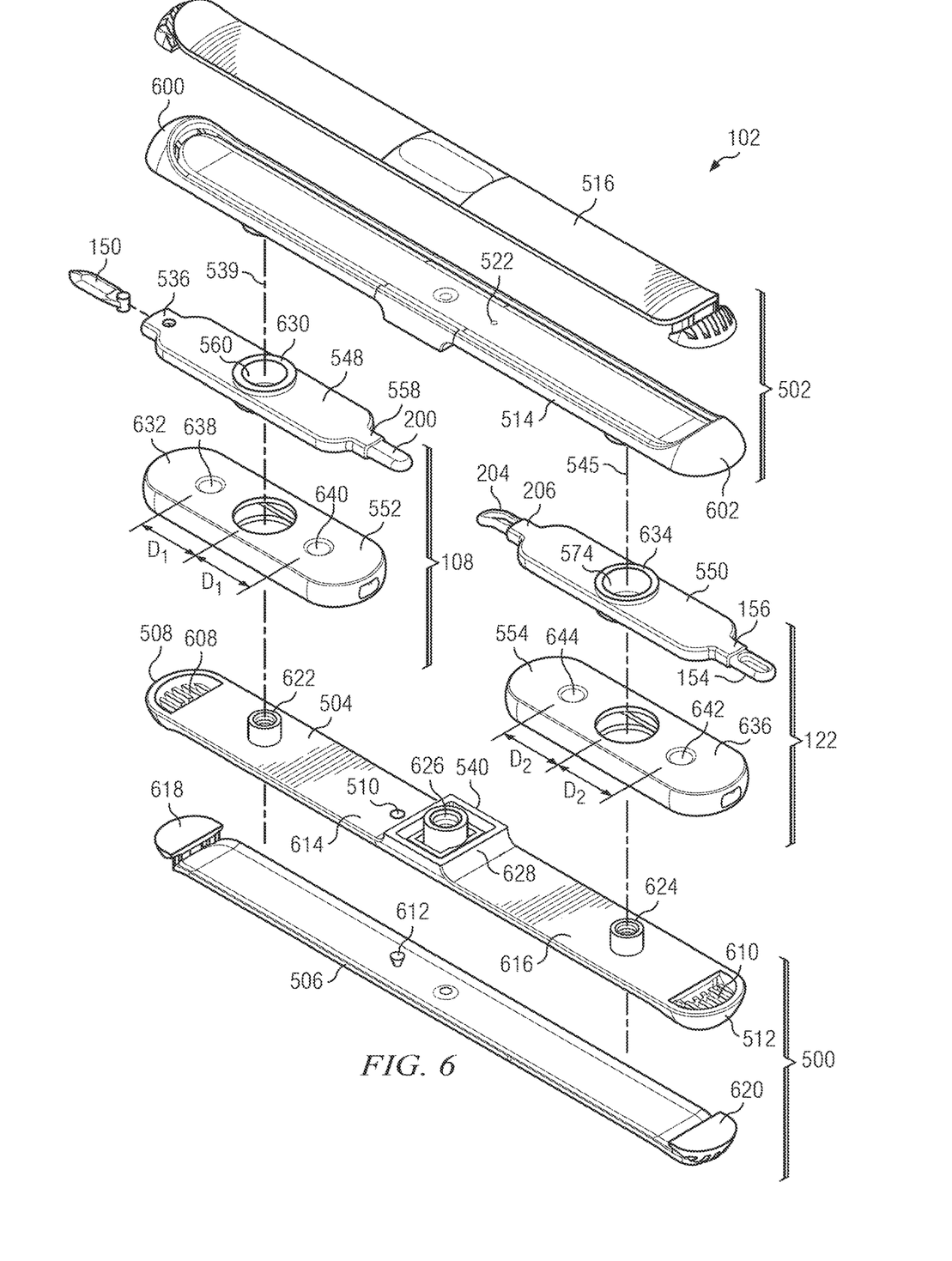
FIG. 6 is a bottom perspective exploded view of the tool shown in FIGS. 1-4.
Figure 7:
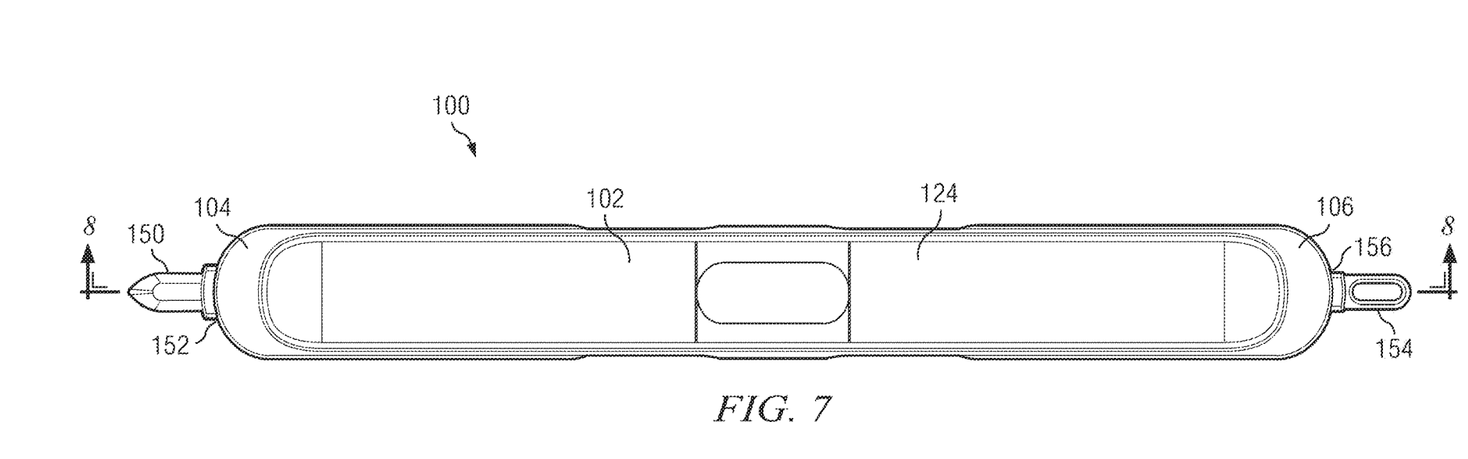
FIG. 7 is a top view of the tool shown in FIGS. 1-4, with first and second tool bodies being shown in respective first use configurations.

Further details of the structure and operation of tool 100 may be discerned from the exploded views of FIGS. 5 and 6. The handle 102 may be formed by joining a top handle half 500 and a bottom handle half 502. The top handle half 500 may consist of a plastic substrate or first-shot component 504, and an overmolded or second-shot component 506. In the illustrated embodiment, the overmolded component 506 may not be physically separated from the substrate 504 as the exploded view may suggest. Overmolded component 506 nonetheless has been shown exploded off of handle half substrate 504 to better show the physical features of both, and that is also the case for the other first shot/second shot injection mold components making up tool bodies 108 and 122 and bottom handle half 502.

The first handle half substrate 504 may be molded of a relatively hard plastic polymer such as polypropylene. The overmolded component 506 may be molded of a relatively soft and grippy polymer compound such as a thermoplastic elastomer (TPE) that presents a higher coefficient of friction to objects (such as the fingers of a caregiver) than does the polymer used to mold the handle half substrate 504. The overmolded component 506 is mechanically locked onto the substrate 504 in at least three places: at a first substrate end 508, at a center hole 510 made in substrate 504, and at a second substrate end 512. In each of these places, molten TPE compound is forced through holes in the substrate 504 to mechanically lock the overmolded component 506 to the substrate 504 once the overmolded compound solidifies.

The bottom handle half 502 likewise may be formed from a substrate 514, of a relatively hard plastic polymer compound such as polypropylene, and an overmolded component 516 of a relatively soft and grippy polymer compound, such as a TPE. As per top handle half 500, the overmolded component 516 is injection-molded onto the substrate 514 and in its molten state is forced through holes 518 in a first substrate end 520, through a center hole 522 near the center, and through holes 524 in a second substrate end 526. Once solidified the overmolded component 516 therefore will be mechanically locked onto the bottom half substrate 514. The center mechanical locking hole 522 may be conical, with a smaller bottom end and a larger top end. The molten polymer therefore will make a conical shape 528 when forced into the locking hole 522.

The bottom half substrate component 514 has a planar upper surface 530 that forms most of a bottom surface of first slot 110. The rest of this bottom surface may be formed by a pad 532 that is a portion of the overmolded component 516; the upper surface of pad 532 is coplanar with surface 530. Similarly, the bottom half substrate component 514 has a planar upper surface 534 that forms most of a bottom surface of second slot 118. The rest of this further bottom surface may be formed by a pad 536 that is a portion of the overmolded component 516. The upper surface of pad 536 is coplanar with surface 534.

An inner shaft 538 upwardly extends from surface 530 and is used to form part of an axle for first tool body 108. The shaft 538 is coaxial around first tool body axis 539, and is positioned inwardly from the substrate end 520 but outwardly from a center 540 of the bottom half substrate 514. A first slot detenting structure 542 is formed on surface 530 and is positioned between substrate end 520 and the first tool body axis 539. In the illustrated embodiment, the first slot detenting structure 542 is a bump that is raised relative to the planar surface 530. The center or axis of first slot detenting structure 542 is positioned at a first distance $D_1$ from the first tool body axis 539.

Similarly, an inner shaft 544 extends upwardly from surface 534, is positioned around second tool body axis 545 and is used to form part of an axle for the second tool body 122. The inner shaft 544 is positioned inwardly from substrate end 526, and therefore inwardly from the end 106 of the assembled handle 102, but outwardly from the center 540 of the bottom half substrate 514 and therefore outwardly from the center 114 of the completed handle 102. Axes 539 and 545 are at an angle to handle axis X, and preferably are 90 degrees thereto. In the illustrated embodiment, axes 539 and 545 are parallel to each other, but in other embodiments they could be at an angle to each other.

A second slot detenting structure 546 is positioned outwardly from center 540, as well as from inner shaft 544, but inwardly from substrate end 526. In the illustrated embodiment the detenting structure 546 is an eminence or bump, and has a raised surface relative to planar surface 534. The center of detenting structure 546 is located at a second distance $D_2$ from the second tool body axis 545. In the illustrated embodiment first distance $D_1$ is the same as second distance $D_2$, but they may be chosen to be different. Distances $D_1$ and $D_2$ can be chosen to be in the range of about 0.5 to about 2.2 cm, and in one embodiment are 1.235 cm.

At the center 540 of bottom half handle substrate 514 is formed an upstanding male snap connector 547. This is surrounded by an upstanding square male wall flange 549. Connector 547 and wall flange 549 are used to assemble the bottom handle half 502 to the top handle half 500, in a manner described below.

In the illustrated embodiment, each of the tool bodies 108 and 122 comprises a substrate 548, 550, around which is overmolded a jacket 552, 554. The tool body substrates 548, 550 can be molded, in a first-shot step, from a relatively hard polymer compound such as polypropylene. In a second-shot step, a relatively soft polymer such TPU or another TPE is overmolded on the substrate 548, 550.

Tool body 108 further has a third, harder component: The first tool head 150 may be a pick that is meant to remove debris from underneath an infant's nails and can be molded of a polymer, such as nylon, that is harder than the polymer used to mold the rest of the tool body substrate 548. After its molding, tool head 150 may then be clamped into a first-shot mold, and the second polymer molded partially around it, thereby becoming mechanically locked to the first tool body substrate 548. After that, the first tool body jacket 552 may be overmolded onto the workpiece using a third polymer.

Jacket 552 will cover most of the surface area of first tool body substrate 548. Exceptions are first and second substrate ends 556 and 558, which can be used as shutoff surfaces for the overmolded material. The tool head 200 is molded as an extension of substrate end 558 and in this embodiment is in the nature of a straight loop that has general application for cleaning and grooming an infant. In the illustrated embodiment, tool heads 154, 200, 204 are formed of the same polymer used to form tool body substrates 548, 550, and therefore may be integrally molded with them. In other embodiments, one or more of the tool heads may be overmolded with a soft polymer such as a TPU.

First tool body substrate 548 has, at its center, a cylindrical first axle hole 560 that in use is coaxial with first tool body axis 539. The axle hole 560 extends from the top surface of substrate 548 to the bottom surface thereof and presents a bearing surface in contact with the surface of outer shaft 622 (described below). An upstanding top annulus 562 of the first tool body substrate 548 surrounds axle hole 560, will remain uncovered by overmolded jacket 552 and acts as an overmold shutoff surface.

The first tool body jacket 552 forms a top surface 564 of the completed first tool body 108. A top surface of annulus 562 is coplanar with top surface 564 of jacket 552. The top surface 564 may be used as a space to display indicia to indicate a suggested use of each of the tool heads. Since the illustrated pick 150 is meant to clean an infant's nails, indicium 566 is in the nature of a baby's hand. Since straight loop 200 has a more general application, an indicium 568 is a schematic image of a whole baby. These indicia become visible when the user rotates tool body 108 from either its first use configuration or its second use configuration, such that the long axis of tool body 108 is no longer parallel with handle axis X, and such that the indicia are outside of the first slot 110 and are no longer obscured by handle 102.

The construction of second tool body 122 can be similar. A second tool body substrate 550 may have a third end 570 and, opposed to third end 570, a fourth end 572. Ends 570, 572 include shutoff surfaces limiting the coverage of the overmolded TPU jacket 554. The second tool body substrate 550 may be molded of a relatively hard plastic such as polypropylene and third and fourth tool heads 154, 204 may be integrally molded with it. The third tool head 154 may be in the nature of a scoop or bowl while the fourth tool head 204 may be in the nature of a curved loop. Tool heads other than the pick, straight loop, curved loop and scoop shown could be used on respective ends of the tool bodies. Further, the tool heads could be of sizes, shapes and dimensions other than those shown.

The second tool body jacket 554 will cover most of the surface area of second tool body substrate 550, with the exception of the third and fourth tool heads 154, 204 and a second axle hole 574. The second axle hole 574 presents a cylindrical bearing surface that engages the cylindrical surface of a second outer shaft 624 (described below). In use, the second axle hoe 574 is coaxial with second tool body axis 545. A top annulus 576 upwardly extends from the rest of the top surface of second tool body substrate 550, surrounds second axle hole 574 and may be used as a shutoff surface to provide a barrier to the molten second-shot material.

The second tool body jacket 554 forms a top surface 578 of the second tool body 122. A top surface of the annulus 576 will be coplanar with top surface 578 once the second tool body 122 is completely molded. A nose indicium 580 may be formed on top surface 578 to suggest a use for the adjacent fourth tool head 204: to clean out mucus from an infant's nose. An ear indicium 582 may be formed on top surface 578, near third tool head 154, to suggest that tool head 154 be used to remove ear wax from an infant's ear, using a scooping action. These indicia may be viewed by the user when the user rotates tool body 122 away from either its first use configuration or its second use configuration, similar to the case for indicia 566 and 568, such that the tool body 122 is no longer aligned with handle axis X and such that indicia 580 and 582 are no longer covered up by the handle 102.

Turning now to FIG. 6, an exploded perspective bottom view, the substrate 514 of the bottom handle half 502 has a first end 600 and an opposed second end 602. Molten polymer making up the overmolded top handle half component 516 is forced through holes 518, 524 (FIG. 5) in the first and second substrate ends 600, 602 to anchor the overmolded component 516 to the substrate 514. The center hole 522 is shown to have a small diameter at its lower end to mechanically lock overmolded component 516 to substrate 514 at that point.

The substrate 504 of the top handle half 500 has holes 608 near its first end 508, and holes 610 near its second end 512. Molten polymer making up the overmolded top half component 506 is forced through holes 608, 610 and center hole 510 to mechanically lock the overmolded component 506 onto substrate 504. As solidified, a downwardly depending cone 612 will occupy lock hole 510.

The top handle half substrate 504 has a planar surface 614 near first end 508 and a planar surface 616 near its second end 512. Surface 614, in combination with pad 618 of the overmolded component 506, constitute a planar upper surface of the first slot 110 when the handle halves 500, 502 are assembled to each other. Similarly, surface 616, in combination with a pad 620 of the overmolded component 506, constitute a planar upper surface of the second slot 118 when the handle halves 500, 502 are assembled to each other.

A first outer shaft 622 is coaxial to first tool body axis 539 and downwardly depends from surface 614. The first outer shaft 622 has a cylindrical surface which will be engaged by axle hole 560. A second outer shaft 624 is coaxial to second tool body axis 545 and downwardly depends from surface 616. The second outer shaft 624 has a cylindrical surface which will be engaged by axle hole 574 when the tool body 122 is assembled to the handle 102. A female snap connector 626 is located at the center of the first handle half substrate 504. A four-sided female wall flange 628 surrounds, and is spaced from, the snap connector 626.

An annulus 630 terminates the lower end of axle hole 560 and downwardly extends from a lower surface of first tool body substrate 548. When first tool body jacket 552 is overmolded onto substrate 548, a lower surface of the annulus 630 will be coplanar with a lower surface 632 of the first tool body jacket 552. The annulus 630 acts as a shutoff surface to the molten polymer making up jacket 552. Similarly, an annulus 634 terminates the lower end of axle hole 574 and downwardly extends from a lower surface of the second tool body substrate 550. When second tool body jacket 554 is overmolded around second tool body substrate 550, a lower surface of annulus 634 will be coplanar with a lower surface 636 of the second tool body jacket 552. The annulus 634 acts as a shutoff surface to the molten polymer making up jacket 554.

In the illustrated embodiment, a first tool body detent structure 638 is formed as a circular depression, with a beveled sidewall, in the lower surface 632 of the first tool body jacket 552. The center of the first tool body detent structure 638 is positioned at the first distance $D_1$ from first tool body axis 539. Conveniently, the first tool body detent structure 638 may be formed as a hole in the tool body jacket 552, but without any dimple or hole in the underlying surface of first tool body substrate 548. The first tool body detent structure 638 is disposed between axis 539 and first tool body end 536. Similarly, a second tool body detent structure 640 may be formed as a circular depression, with a beveled sidewall, in the lower surface 632 of the first tool body jacket 552. The center of the second tool body detent structure 640 is located at distance $D_1$ from first tool body axis 539, in a direction opposite that of first tool body detent structure 638. The second tool body detent structure 640 may be formed as a hole through the jacket 552, but may not include any hole or dimple in the underlying surface of first tool body substrate 548. The second tool body detent structure is disposed between first tool body axis 539 and second tool body end 558.

A third tool body detenting structure 642 may be formed as a circular depression in the lower surface 636 of overmolded jacket 554 of the second tool body 122. The detenting structure 642 is disposed between third tool body end 156 and the second tool body axis 545, and its center is disposed at the distance $D_2$ from axis 545. Detenting structure 642 conveniently may be formed as a hole in jacket 554, with a beveled edge, but not to include any hole or dimple in the underlying surface of second tool body substrate 550. Similarly, a fourth tool body detenting structure 644 may be formed as a circular depression in lower surface 636. The fourth tool body detenting structure 644 is disposed between fourth tool body end 206 and second tool body axis 545, such that its center is located at the distance $D_2$ from axis 545. It also conveniently may be formed as hole extending completely through the jacket 554, with a beveled edge, but not to include any hole or dimple in the underlying surface of second tool body substrate 550. The beveled edges or sidewalls of the tool body detenting structures 638, 640, 642 and 644 are camming surfaces allowing the slot detent structures 542, 546 to cam in and out of the use positions defined by the detents.

While in the illustrated embodiment the tool body detenting structures are shown as depressions and the slot detenting structures are shown as bumps, this could be reversed in other embodiments. Further, the illustrated embodiment forms the tool body detenting structures 638, 640, 642, 644 only in the lower surfaces of tool bodies 108 and 122, and these interact with detenting structures 542, 546 in the lower surfaces of slots 110, 118. In other embodiments, mating detenting structures could be formed in both the top and bottom surfaces of tool bodies 108 and 122, as interacting with slot detenting structures in both the upper and lower surfaces of the slots.

Figure 8:
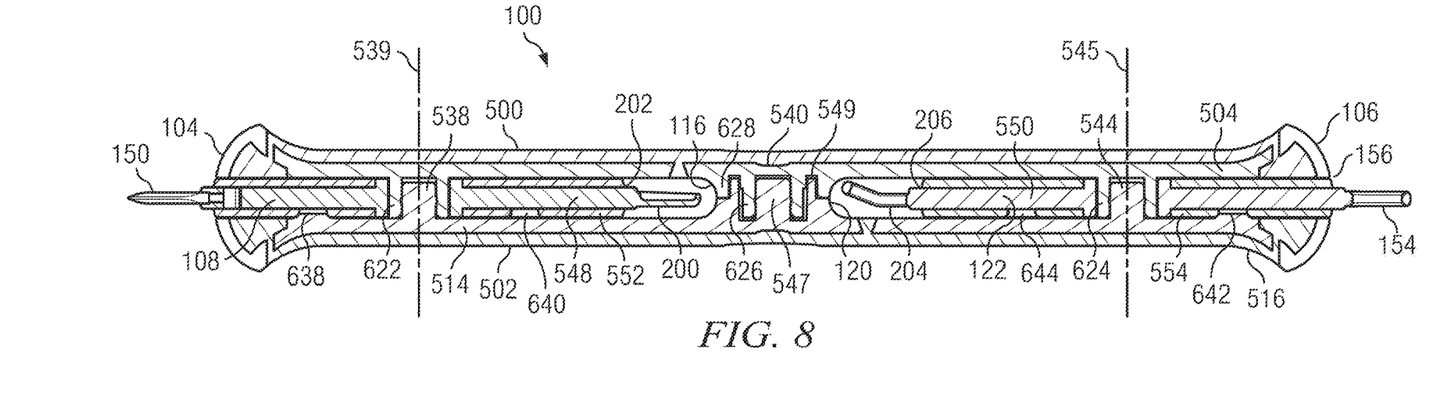
FIG. 8 is an axial sectional view taken substantially along line 8-8 of FIG. 7.

The assembly of the tool 100 can best be understood with reference to FIG. 8. Prior to assembly, the polymer making up first tool body substrate 548 is molded around an end of first tool head 150. The first tool body jacket 552 is then overmolded onto the first tool body substrate 548 to complete tool body 108. The second tool body jacket 554 is overmolded onto the second tool body substrate 550. The preferably TPE component 506 of the top handle half is overmolded onto and through the top handle half substrate 504 to complete the top handle half 500. The preferably TPE component 516 of the bottom handle half is overmolded onto and through the bottom handle half substrate 514 to complete the bottom handle half 502. The top handle half 500 is placed upside down. Tool body 108 is fitted onto outer shaft 622 while tool body 122 is fitted onto outer shaft 624. Then the bottom handle half 502 is joined to the top handle half 500 by snapping inner shaft 538 into outer shaft 622, male connector 547 into female connector 626, male wall flange 549 into female wall flange 628, and inner shaft 544 into outer shaft 624.

After assembly, the first tool body 108 is mounted in the first slot 110 and is rotatable around first tool body axis 539 while second tool body 122 is mounted in the second slot 118 and is rotatable around second tool body axis 545. During rotation of tool body 108, its upper surface 564 will slide along upper surface 614, 618 of slot 110, while its lower surface 632 will slide along lower surface 530, 532 of slot 110. During rotation of tool body 122, its upper surface 578 will slide along upper surface 616, 620 of slot 118, while its lower surface 636 will slide along lower surface 534, 536 of slot 118.

When tool body 108 is rotated to its first use position, the first slot detenting structure 542 will cam into the first tool body detenting structure 638. First slot detenting structure 542 will create a predetermined amount of resistance to any torsional force around axis 539 that is urging tool body 108 out of the first use position. Similar resistance to angular movement will be encountered by the user when the first tool body 108 assumes its second use position, at which time the first slot detent structure 542 cams into the second tool body detenting structure 640. When the second tool body 122 assumes either its first use configuration or its second use configuration by the camming action of second slot detenting structure 546 with a respective one of second tool body detenting structures 642 or 644, there will also be a predetermined amount of resistance to any torsional force attempting to turn tool body 122 out of these use positions. In this way, the tool bodies 108, 122 will not inadvertently depart from their alignment with handle axis X while an extracting or grooming operation is underway.

In summary, a multihead grooming and cleaning tool has been described that provides the user with four different tool heads. Two of the heads are shrouded in the handle while two of the heads are deployed to respective use positions. Detent structures in the handle slots and in the tool bodies act to maintain the tool bodies in either first or second use configurations during a grooming operation.

While embodiments of the present invention have been described above and illustrated in the appended drawings, the present invention is not limited thereto but only by the scope and spirit of the appended claims.

We claim:

1. A multiheaded tool for extracting debris from different orifices of a human, the tool comprising:
    an elongate handle having a first handle end and a second handle end opposed to the first handle end, the handle disposed on a handle axis between the first handle end and the second handle end, a handle center of the handle located on the handle axis and disposed between the first handle end and the second handle end;
    an elongate first slot opening on the first handle end and extending toward the handle center, the first slot having a top surface and a bottom surface spaced from the top surface, a first tool body axis extending from the top surface of the first slot to the bottom surface of the first slot and disposed at an angle to the handle axis, the first tool body axis spaced from the first handle end and from the handle center, a first slot detent structure formed on at least one of the top and bottom surfaces of the first slot and to be spaced from the first tool body axis by a first distance;
    an elongate first tool body mounted in the first slot and having a first tool body end and a second tool body end opposed to the first tool body end, the first tool body rotatable around the first tool body axis, a top surface of the first tool body extending from the first tool body end to the second tool body end and disposed in sliding relation to the top surface of the first slot, a bottom surface of the first tool body extending from the first tool body end to the second tool body end and disposed in sliding relation to the bottom surface of the first slot;
    a first tool body detent structure formed on at least a preselected one of the top surface of the first tool body and the bottom surface of the first tool body and formed at the first distance from the first tool body axis, a second tool body detent structure formed on the preselected one of the top surface of the first tool body and the bottom surface of the first tool body and formed at the first distance from the first tool body axis, wherein
    in a first use configuration of the first tool body, the first tool body detent structure interacts with the first slot detent structure to create resistance to torque exerted on the first tool body around the first tool body axis, a first tool head affixed to the first tool body end then being deployed for use in a position beyond the first handle end and a second tool head affixed to the second tool body end being shrouded by the handle, and
    in a second use configuration of the first tool body, the second tool body detent structure interacts with the first slot detent structure to create resistance to torque exerted on the first tool body around the first tool body axis, the second tool head then being deployed for use in a position beyond the first handle end and the first tool head being shrouded by the handle,
    wherein the first tool body comprises a substrate molded out of a first polymer and an overmolded component molded out of a second polymer softer than the first polymer, the overmolded component forming the top and bottom surfaces of the first tool body, the depressions being formed only in the overmolded component.

2. A multiheaded tool for extracting debris from different orifices of a human, the tool comprising:
    an elongate handle having a first handle end and a second handle end opposed to the first handle end, the handle disposed on a handle axis between the first handle end and the second handle end, a handle center of the handle located on the handle axis and disposed between the first handle end and the second handle end;
    an elongate first slot opening on the first handle end and extending toward the handle center, the first slot having a top surface and a bottom surface spaced from the top surface, a first tool body axis extending from the top surface of the first slot to the bottom surface of the first slot and disposed at an angle to the handle axis, the first tool body axis spaced from the first handle end and from the handle center, a first slot detent structure formed on at least one of the top and bottom surfaces of the first slot and to be spaced from the first tool body axis by a first distance;
    an elongate first tool body mounted in the first slot and having a first tool body end and a second tool body end opposed to the first tool body end, the first tool body rotatable around the first tool body axis, a top surface of the first tool body extending from the first tool body end to the second tool body end and disposed in sliding relation to the top surface of the first slot, a bottom surface of the first tool body extending from the first tool body end to the second tool body end and disposed in sliding relation to the bottom surface of the first slot;

a first tool body detent structure formed on at least a preselected one of the top surface of the first tool body and the bottom surface of the first tool body and formed at the first distance from the first tool body axis, a second tool body detent structure formed on the preselected one of the top surface of the first tool body and the bottom surface of the first tool body and formed at the first distance from the first tool body axis, wherein in a first use configuration of the first tool body, the first tool body detent structure interacts with the first slot detent structure to create resistance to torque exerted on the first tool body around the first tool body axis, a first tool head affixed to the first tool body end then being deployed for use in a position beyond the first handle end and a second tool head affixed to the second tool body end being shrouded by the handle, and in a second use configuration of the first tool body, the second tool body detent structure interacts with the first slot detent structure to create resistance to torque exerted on the first tool body around the first tool body axis, the second tool head then being deployed for use in a position beyond the first handle end and the first tool head being shrouded by the handle, wherein the first tool head is molded of a first polymer, the first tool body molded around a portion of the first tool head and of a second polymer softer than the first polymer.

3. A multiheaded tool for extracting debris from different orifices of a human, the tool comprising:

an elongate handle having a first handle end and a second handle end opposed to the first handle end, the handle disposed on a handle axis between the first handle end and the second handle end, a handle center of the handle located on the handle axis and disposed between the first handle end and the second handle end;

an elongate first slot opening on the first handle end and extending toward the handle center, the first slot having a top surface and a bottom surface spaced from the top surface, a first tool body axis extending from the top surface of the first slot to the bottom surface of the first slot and disposed at an angle to the handle axis, the first tool body axis spaced from the first handle end and from the handle center, a first slot detent structure formed on at least one of the top and bottom surfaces of the first slot and to be spaced from the first tool body axis by a first distance;

an elongate first tool body mounted in the first slot and having a first tool body end and a second tool body end opposed to the first tool body end, the first tool body rotatable around the first tool body axis, a top surface of the first tool body extending from the first tool body end to the second tool body end and disposed in sliding relation to the top surface of the first slot, a bottom surface of the first tool body extending from the first tool body end to the second tool body end and disposed in sliding relation to the bottom surface of the first slot;

a first tool body detent structure formed on at least a preselected one of the top surface of the first tool body and the bottom surface of the first tool body and formed at the first distance from the first tool body axis, a second tool body detent structure formed on the preselected one of the top surface of the first tool body and the bottom surface of the first tool body and formed at the first distance from the first tool body axis, wherein in a first use configuration of the first tool body, the first tool body detent structure interacts with the first slot detent structure to create resistance to torque exerted on the first tool body around the first tool body axis, a first tool head affixed to the first tool body end then being deployed for use in a position beyond the first handle end and a second tool head affixed to the second tool body end being shrouded by the handle, and in a second use configuration of the first tool body, the second tool body detent structure interacts with the first slot detent structure to create resistance to torque exerted on the first tool body around the first tool body axis, the second tool head then being deployed for use in a position beyond the first handle end and the first tool head being shrouded by the handle, the handle comprising a top half and a bottom half, a lower surface of the top half forming the top surface of the first slot, an upper surface of the bottom half forming the bottom surface of the first slot;

wherein the top half of the handle comprises a top half substrate molded of a first polymer and a top half overmolded component molded of a second polymer having a higher coefficient of friction than the first polymer, the second polymer injected through holes in the top half substrate such that the top half overmolded component is mechanically locked to the top half substrate, the bottom half of the handle comprising a bottom half substrate molded of the first polymer and a bottom half overmolded component molded of the second polymer, the second polymer injected through holes in the in the bottom half substrate such that the bottom half overmolded component is mechanically locked to the bottom half substrate.

4. A multiheaded tool for extracting debris from different orifices of a human, the tool comprising:

an elongate handle having a first handle end and a second handle end opposed to the first handle end, the handle disposed on a handle axis between the first handle end and the second handle end, a handle center of the handle located on the handle axis and disposed between the first handle end and the second handle end;

an elongate first slot opening on the first handle end and extending toward the handle center, the first slot having a top surface and a bottom surface spaced from the top surface, a first tool body axis extending from the top surface of the first slot to the bottom surface of the first slot and disposed at an angle to the handle axis, the first tool body axis spaced from the first handle end and from the handle center, a first slot detent structure formed on at least one of the top and bottom surfaces of the first slot and to be spaced from the first tool body axis by a first distance;

an elongate first tool body mounted in the first slot and having a first tool body end and a second tool body end opposed to the first tool body end, the first tool body rotatable around the first tool body axis, a top surface of the first tool body extending from the first tool body end to the second tool body end and disposed in sliding relation to the top surface of the first slot, a bottom surface of the first tool body extending from the first tool body end to the second tool body end and disposed in sliding relation to the bottom surface of the first slot;

a first tool body detent structure formed on at least a preselected one of the top surface of the first tool body and the bottom surface of the first tool body and formed at the first distance from the first tool body axis, a second tool body detent structure formed on the preselected one of the top surface of the first tool body and the bottom surface of the first tool body and formed at the first distance from the first tool body axis, wherein in a first use configuration of the first tool body, the first tool body detent structure interacts with the first slot detent structure to create resistance to torque exerted on the first tool body around the first tool body axis, a first tool head affixed to the first tool body end then being deployed for use in a position beyond the first handle end and a second tool head affixed to the second tool body end being shrouded by the handle, and in a second use configuration of the first tool body, the second tool body detent structure interacts with the first slot detent structure to create resistance to torque exerted on the first tool body around the first tool body axis, the second tool head then being deployed for use in a position beyond the first handle end and the first tool head being shrouded by the handle, a first tool body shaft formed on the first tool body axis to extend from the top surface of the first slot and the bottom surface of the first slot, the first tool body comprising a first tool body substrate molded of a first polymer and an overmolded first tool body jacket formed of a second polymer softer than the first polymer, the first tool body substrate having a first bearing surface engaging the first tool body shaft, the first bearing surface of the first tool body extending through the first tool body substrate between the top surface of the first tool body and the bottom surface of the first tool body, the first tool body substrate further having a top raised ring formed on the top surface of the first tool body to be adjacent to the first bearing surface and a bottom raised ring formed on the bottom surface of the first tool body to be adjacent to the first bearing surface, the top and bottom raised rings of the first tool body substrate acting as shutoff surfaces during the overmolding of the first tool body jacket onto the first tool body substrate.

5. A multiheaded tool for extracting debris from different orifices of a human, the tool comprising:

an elongate handle having a first handle end and a second handle end opposed to the first handle end, the handle disposed on a handle axis between the first handle end and the second handle end, a handle center of the handle located on the handle axis and disposed between the first handle end and the second handle end;

an elongate first slot opening on the first handle end and extending toward the handle center, the first slot having a top surface and a bottom surface spaced from the top surface, a first tool body axis extending from the top surface of the first slot to the bottom surface of the first slot and disposed at an angle to the handle axis, the first tool body axis spaced from the first handle end and from the handle center, a first slot detent structure formed on at least one of the top and bottom surfaces of the first slot and to be spaced from the first tool body axis by a first distance;

an elongate first tool body mounted in the first slot and having a first tool body end and a second tool body end opposed to the first tool body end, the first tool body rotatable around the first tool body axis, a top surface of the first tool body extending from the first tool body end to the second tool body end and disposed in sliding relation to the top surface of the first slot, a bottom surface of the first tool body extending from the first tool body end to the second tool body end and disposed in sliding relation to the bottom surface of the first slot;

a first tool body detent structure formed on at least a preselected one of the top surface of the first tool body and the bottom surface of the first tool body and formed at the first distance from the first tool body axis, a second tool body detent structure formed on the preselected one of the top surface of the first tool body and the bottom surface of the first tool body and formed at the first distance from the first tool body axis, wherein in a first use configuration of the first tool body, the first tool body detent structure interacts with the first slot detent structure to create resistance to torque exerted on the first tool body around the first tool body axis, a first tool head affixed to the first tool body end then being deployed for use in a position beyond the first handle end and a second tool head affixed to the second tool body end being shrouded by the handle, and in a second use configuration of the first tool body, the second tool body detent structure interacts with the first slot detent structure to create resistance to torque exerted on the first tool body around the first tool body axis, the second tool head then being deployed for use in a position beyond the first handle end and the first tool head being shrouded by the handle, wherein the handle has a length between the first and second handle ends, a top surface, and a bottom surface opposed to the top surface, the handle having a uniform first thickness between the top surface of the handle and the bottom surface of the handle throughout most of the length of the handle, the first handle end having an enlarged thickness relative to the first thickness, the first handle end acting as a stop to prevent overpenetration of the first tool head or the second tool head into an orifice of the human.

* * * * *